Figure 1:
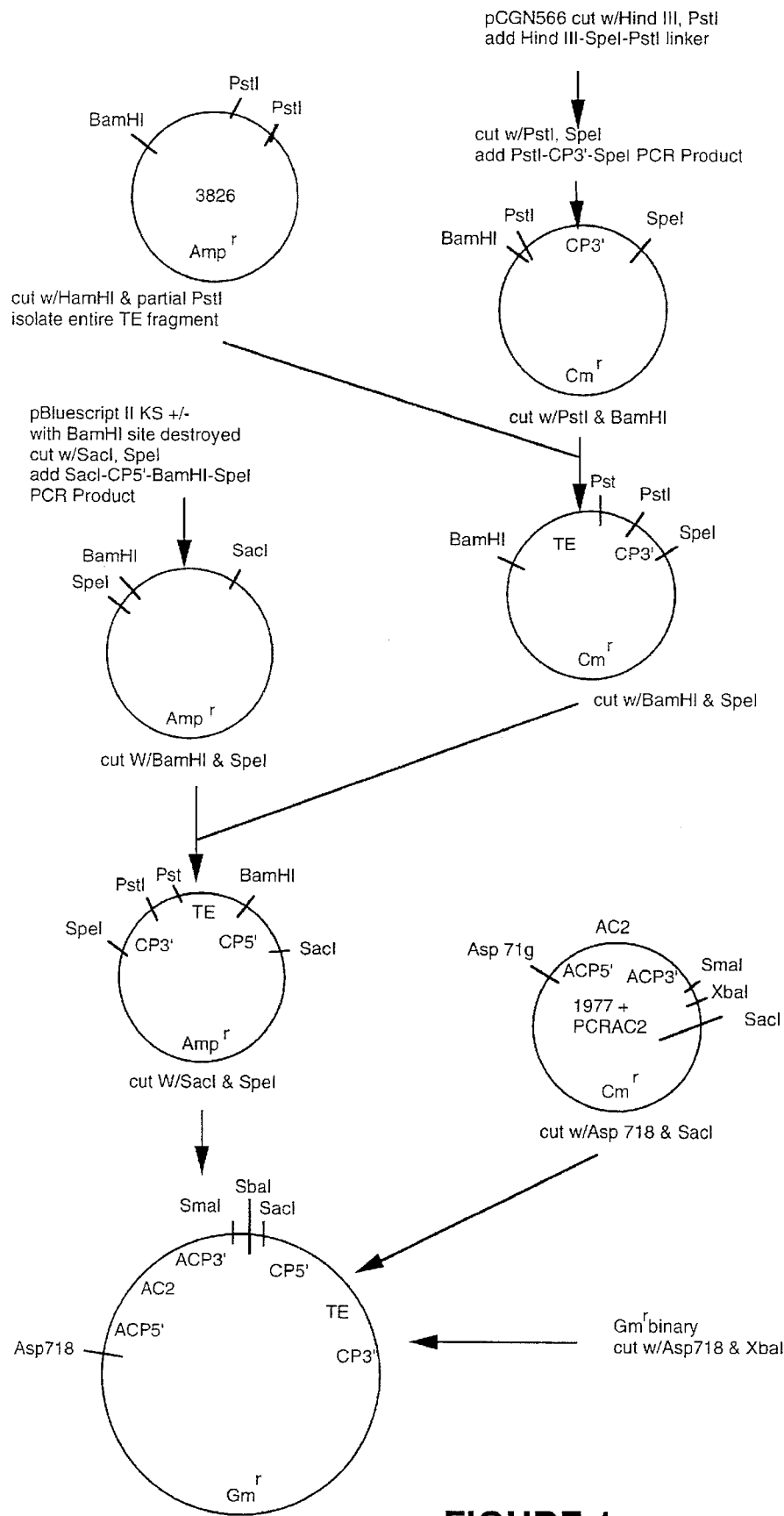

US005650303A

United States Patent [19]
Kridl et al.

[11] Patent Number: 5,650,303
[45] Date of Patent: Jul. 22, 1997

[54] GEMINIVIRUS-BASED GENE EXPRESSION SYSTEM

[75] Inventors: Jean C. Kridl; George Bruening, both of Davis; Vic C. Knauf, Winters, all of Calif.

[73] Assignees: Calgene, Inc., Davis; The Regents of the University of California, Oakland, both of Calif.

[21] Appl. No.: 24,164

[22] Filed: Feb. 26, 1993

[51] Int. Cl.$^6$ .............................. C12N 5/04; C12N 15/64; C12N 15/82

[52] U.S. Cl. ................................. 435/91.41; 435/91.42; 435/240.4; 435/320.1

[58] Field of Search ........................... 435/69.1, 172.3, 435/235.1, 240.4, 320.1, 91.4, 91.41, 91.42, 240.2; 536/23.1, 23.72

[56] References Cited

U.S. PATENT DOCUMENTS

| | | | |
|---|---|---|---|
| 4,801,540 | 1/1989 | Hiatt et al. | 435/172.3 |
| 4,943,674 | 7/1990 | Houck et al. | 800/205 |

FOREIGN PATENT DOCUMENTS

| | | |
|---|---|---|
| 0 120 516 | 10/1984 | European Pat. Off. |
| 0 221 044 | 5/1987 | European Pat. Off. |
| 0 255 378 | 2/1988 | European Pat. Off. |
| 0 298 918 | 1/1989 | European Pat. Off. |
| 0 393 690 | 10/1990 | European Pat. Off. |
| 0 425 004 | 5/1991 | European Pat. Off. |
| WO 88-09334 | 12/1988 | WIPO |
| WO 90/04063 | 4/1990 | WIPO |
| WO 91/02958 | 3/1991 | WIPO |
| WO 91/13078 | 9/1991 | WIPO |
| WO 91/13972 | 9/1991 | WIPO |
| WO 91/13980 | 9/1991 | WIPO |
| WO 91/13994 | 9/1991 | WIPO |
| WO 91/16421 | 10/1991 | WIPO |
| WO 91/19808 | 12/1991 | WIPO |
| WO 92/03564 | 3/1992 | WIPO |
| WO 92/15675 | 9/1992 | WIPO |

OTHER PUBLICATIONS

Morris et al. "Mutagenesis of the AC3 Open Reading Frame of African Cassava Mosaic Virus DNA A Reduces DNA B Replication and Ameliorates Disease Symptoms", J. Gen Virol. 1991, vol. 72, pp. 1205–1213.

Kridl et al. "Transcriptional Regulatory Sequences from Plant Viruses", 1986, Bio Essays, vol. 4(1), pp. 4–8.

Zhan et al. "Analysis of the Potential Promoter Sequences of African Cassava Mosaic Virus by Transient Expression of the β-glucuronidase Gene", 1991, J. Gen. Virol., vol. 72, pp. 2849–2852.

Haley, et al. "Regulation of the Activities of African Cassava Mosaic Virus Promoters by the AC1, AC2 and AC3 Gene Products" Virology (Jun. 1992) Vol. 188, No. 2 905–909.

Etessami, et al., "Mutational Analysis of Complementary–Sense Gene of African Cassava Mosaic Virus DNA A" Biological Abstracts (1991) vol. 2 Abstract No. 36062.

Journal General Virology (1991), vol. 72 No. 5 1005–1012.

Meyer, et al. "The Use of African Cassava Mosaic Virus as a Vector System for Plants" Gene (1992) vol. 110; 213–217.

Sunter, et al "Transactivation of Geminivirus AR1 and BR1 Gene Expression by the Viral AL2 Gene Product Occurs at the Level of Transcription" The Plant Cell (Oct. 1992) vol. 4, No. 10 1321–1331.

Radke et al., "Transformation of *Brassica napus* L. using *Agrobacterium tumefaciens*: Developmentally Regulated Expression of a Reintroduced Napin Gene", Theor. Appl. Genet. (1988) 75:685–694.

Coutts et al., "Development of Geminivirus–based Gene Vectors for Dicotyledonous Plants", Aust. J. Plant Physiol., 17:365–375 (1990).

Haley et al., "Regulation of the Activities of African Cassava Mosaic Virus Promoters by the AC1, AC2 and AC3 Gene Products", Virology, 188:905–909 (1992).

Brough et al., "Kinetics of Tomato Golden Mosaic Virus DNA Replication and Coat Protein Promoter Activity in *Nicotiana tabacum* Protoplasts", Virology, 187:1–9 (1992).

Sunter and Bisaro, "Transactivation in a Geminivirus AL2 Gene Product is Needed for Coat Protein Expression", Virology, 180:461–419 (1991).

Sunter et al., "Genetic Analysis of Tomato Golden Mosaic Virus:ORF AL2 is Required for Coat Protein Accumulation while ORF AL3 is Necessary for Efficient DNA Replication", Virology, 179:69–77 (1990).

Kridl et al., "Isolation and Characterization of an Expressed Napin Gene from *Brassica rapa*", Seed Science Research, 1:209–219 (1991).

John and Crow, "Gene Expression in Cotton (*Gossypium hirsutum* L.) Fiber: Cloning of the mRNAs", PNAS (USA), 89:5769–5773 (1992).

Mansson et al., "Characterization of Fruit Specific cDNAs from Tomato", Mol. Gene Genet., 200:356–361 (1985).

Slater et al., "Isolation and Characterization of cDNA Clones for Tomato Polygalacturonase and Other Ripening–related Proteins", Plant Mol. Biol., 5:137–147 (1985).

Piechulla et al., "Expression of Nuclear and Plastid Genes for Photosynthesis–specific Proteins During Tomato Fruit Development and Ripening", Plant Molec. Biol., 7:367–376 (1986).

Gasser, et al. "Isolation of Tissue–Specific cDNAs from Tomato Pistils", Plant Cell, 1:15–24 (1989).

Graham et al., "Wound–induced Proteinase Inhibitors from Tomato Leaves", J. Biol. Chem., 260:6561–6554 (1985).

Smith et al., "Rapid Appearance of an mRNA Correlated with Ethylene Synthesis Encoding a Protein of Molecular Weight 35000", Planta, 168:94–100 (1986).

Graham et al., "Accumulation of a Metallo–carboxypeptidase Inhibitor in Leaves of Wounded Potato Plants", Biochem. Biophys. Res. Comm., 101:1164–1170 (1981).

Radke et al., "Transformation and Regeneration of *Brassica rapa* using *Agrobacterium tumefaciens*", Plant Cell Reports, 11:499–505 (1992).

McCormick et al., "Leaf Disc Transformation of Cultivated Tomato (*L. esculentum*) using *Agrobacterium tumefaciens*", Plant Cell Reports, 5:81–84 (1986).

Fillatti et al., "Efficient Transfer of a Glyphosate Tolerance Gene into Tomato using a Binary *Agrobacterium tumefaciens* Vector", Bio/Technology, 5:726–730 (1987).

Harrison, "Advances in Geminivirus Research", Ann. Rev. Phytopathy, 23:55–82 (1985).

Poulsen and Chua, "Dissection of 5(prime) Upstream Sequences for Selective Expression of the *Nicotiana plumbaginifolia* rbcS–8B Gene", *Mol. Gen. Genet.*, 214:16–23 (1988).

Benfey et al., "Tissue–specific Expression from CaMV 35S Enhancer Subdomains in Early Stages of Plant Development", *EMBO J.*, 9:1677–1684 (1990).

Benfey et al., "Combinatorial and Synergistic Properties of CaMV 35S Enhances Subdomains", *EMBO J.*, 9:1685–1696 (1990).

Gilmartin et al., "Molecular Light Switches for Plant Genes", *Plant Cell*, 2:369–378 (1990).

Knauf et al., "Genetic Analysis of Host Range Expression by *Agrobacterium*", *Mol. Gen. of the Bacteria–Plant Interaction*, pp. 241–247 (1983).

An et al., "New Cloning Vehicles for Transformation of Higher Plants", *EMBO J.*, 4:277–284 (1985).

Stanley and Gay, "Nucleotide Sequence of Cassava Latent Virus DNA", *Nature*, 301:260–262 (1983).

Scherer et al., "Non–essential Repeats in the Prometer Region of a *Brassica rapa* Acyl Carrier Protein Gene Expressed in Developing Embryos", *Plant Mol. Biology*, 18:591–594 (1992).

McBride and Summerfelt, "Improved Binary Vectors for Agrobacterium–mediated Plant Transformation", *Plant Mol. Biology*, 14:269–276 (1990).

*Primary Examiner*—David Guzo

[57] ABSTRACT

A geminivirus based vector system for obtaining controlled expression of a nucleic acid fragment of interest is disclosed. Tissue specific regulatory regions are identified employing cDNA screening and the resulting tissue specific regulatory regions are manipulated for use in geminivirus constructs to provide for transcription and/or expression of nucleic acid sequences nonindigenous to the geminivirus vector for introduction into plant cells. The vector system may be used to provide transformed plants having cells, tissues or parts with a modified phenotypic property.

19 Claims, 1 Drawing Sheet

GEMINIVIRUS-BASED GENE EXPRESSION SYSTEM

TECHNICAL FIELD

The present invention relates to the introduction of nucleic acid into plant cells using a geminivirus-based vector. More particularly, this invention relates to use of geminivirus vectors which provide for tissue specific expression of a transgene in transfected plant cells.

BACKGROUND

For many applications, it is desirable to be able to control gene expression at a particular stage in the growth of a plant or in a particular plant cell, tissue or part. For this purpose, methods are required which can provide for the desired initiation of transcription or expression in the appropriate cell types and/or at the appropriate time in a plant's development without having serious detrimental effects on plant development and productivity. In general, genetic engineering techniques have been directed to modifying the phenotype of individual prokaryotic and eukaryotic cells, especially in culture. Plant cells have proven more intransigent than other eukaryotic cells, due at least in part to a lack of suitable vector systems.

The geminiviruses are two-component single-stranded plant DNA viruses. They possess a circular single-stranded (ss) DNA as their genome encapsidated in twinned "geminate" icosahedral particles. The encapsidated ss DNAs are replicated through circular double stranded DNA intermediates in the nucleus of the host cell, presumably by a rolling circle mechanism. Viral DNA replication, which results in the stimulation of both single and double stranded viral DNAs in large amounts, involves the expression of only a small number of viral proteins that are necessary either for the replication process itself or facilitates replication or viral transcription. The geminiviruses therefore appear to rely primarily on the machinery of the host to copy their genomes and express their genes.

Geminiviruses are subdivided on the basis of host range in either monocots or dicots and whether the insect vector is a leaf hopper or a white fly species. The molecular analysis of the genome of an increasing number of geminiviruses reinforces this division. All monocot-infecting geminiviruses are transmitted by leaf hoppers and their genome comprises a single ss DNA component about 2.7 kb in size; this type of genome, the smallest known infectious DNA, is typified by wheat dwarf virus which is one of a number from the subgroup that have been cloned and sequenced. By contrast, most members infecting dicot hosts are transmitted by the white fly *Bemisia tabaci* and possess a bipartite genome comprising similarly sized DNAs (usually termed A and B) as illustrated by African cassava mosaic virus (ACMV), tomato golden mosaic virus (TGMV) and potato yellow mosaic virus. For successful infection of plants, both genomic components are required. Beet curly top virus occupies a unique intermediary position between the above two subgroups as it infects dicots but contains only a single genomic component equivalent to DNA A possibly as a result of adaption to leaf hopper transmission.

The bipartite subgroup contains only the viruses that infect dicots. Exemplary is the African Cassava Mosaic Virus (ACMV) genome which comprises two circular single-stranded DNA molecules each of approximately 2.7 kb which contain a homologous region (approximately 200 nucleotides) known as the common region. From sequence and mutational analysis, DNA A is known to encode four open reading frames (ORFs). The ORFs are named according to genome component and orientation relative to the common region, i.e., complementary (c) versus viral (v): AC1, the polymerase gene essential to replication; AC2 is required for virus spread; AC3, is a regulator of DNA replication; and AV1 is the coat protein gene. DNA B has two ORFs, BC1 and BV1, both of which are required for virus spread. The arrangement of the ORFs shows that they are expressed in a bidirectional manner. Five major transcripts have been identified and these map to the AV1, BV1, BC1, and AC1 ORFs, separately and the AC2/AC3 ORFs together. AC2 has been shown to encode a transacting factor that stimulates production of the coat protein gene, AV1.

Another example from the bipartite group is the tomato golden mosaic virus (TGMV) which like ACMV is composed of two circular DNA molecules of the same size, both of which are required for infectivity. Sequence analysis of the two genome components reveals six open reading frames (ORFs); four of the ORFs are encoded by DNA A and two by DNA B. On both components, the ORFs diverge from a conserved 230 nucleotide intergenic region (common region) and are transcribed bidirectionally from double stranded replicative form DNA. The ORFs are named according to genome component and orientation relative to the common region (i.e., left versus right). The AL2 gene product transactivates expression of the TGMV coat protein gene.

There is little sequence analogy between the two DNA components of ACMV and TGMV, except for an almost identical common region of about 200 bases, however, the ORFs in the two genomes are analogous and there is the same requirement for the AL2 gene product for transactivation of the coat protein gene. Inspection of AL2 sequences from several bipartite geminiviruses reveal that this protein has the general features expected of a transacting regulatory protein. It is possible that the requirement for AL2 function delays coat protein expression for a period of time sufficient to allow dsDNA amplification to occur.

Vectors in which the coat protein ORF has been replaced by a heterologous coding sequence have been developed and the heterologous coding sequence expressed from the coat protein promoter. However, since expression of the coat protein is dependent upon synthesis of the transacting regulatory protein, the timing of expression of the heterologous sequence from the coat protein promoter is dependent on the timing of expression of the transacting regulatory protein. Accordingly, it would be of interest to develop vectors in which the timing of the expression of the transacting regulatory protein is altered, thereby altering the timing of expression from the coat protein promoter and thus expression of a heterologous sequence inserted in place of the coat protein ORF.

The A genome component contains all viral information necessary for the replication and encapsidation of viral DNA, while the B component encodes functions required for movement of the virus through the infected plant. The DNA A component of these viruses is capable of autonomous replication in plant cells in the absence of DNA B when inserted as a greater than full length copy into the genome of plant cells, or when a copy is electroporated into plant cells.

Relevant Literature

References relating to geminiviruses include the following: R. H. A. Coutts et al., *Aust. J. Plant Physiol.* (1990) 17:365–75; Ann Haley et al., *Virology* (1992) 188:905–909; Garry Sunter et al., *The Plant Cell* (1992) 4:1321–1331; Clare L. Brough et al., *Virology* (1992) 187:1–9; Garry Sunter et al., *Virology* (1991) 180:416–419; and Garry Sunter et al. (1990) *Virology* (1990) 179:69–77.

Genes which are expressed preferentially in plant seed tissues, such as in embryos or seed coats, have also been reported. See, for example, European Patent Application 87306739.1 (published as 0 255 378 on Feb. 3, 1988) and Kridl et al. (Seed Science Research (1991) 1:209–219).

A class of fruit-specific promoters expressed at or during anthesis through fruit development, at least until the beginning of ripening, is discussed in European Application 88.906296.4, the disclosure of which is hereby incorporated by reference. cDNA clones that are preferentially expressed in cotton fiber have been isolated. One of the clones isolated corresponds to mRNA and protein that are highest during the late primary cell wall and early secondary cell wall synthesis stages. John Crow PNAS (1992) 89:5769–5773. cDNA clones from tomato displaying differential expression during fruit development have been isolated and characterized (Mansson et al., *Mol. Gen. Genet.* (1985) 200:356–361: Slater et al., *Plant Mol. Biol.* (1985) 5:137–147).

Mature plastid mRNA for psbA (one of the components of photosystem II reaches its highest level late in fruit development, whereas after the onset of ripening, plastid mRNAS for other components of photosystem I and II decline to nondetectable levels in chromoplasts (Piechulla et al., *Plant Molec. Biol.* (1986) 7:367–376). Recently, cDNA clones representing genes apparently involved in tomato pollen (McCormick et al., *Tomato Biotechnology* (1987) Alan R. Liss, Inc., N.Y.) and pistil (Gasser et al., *Plant Cell* (1989), 1:15–24) interactions have also been isolated and characterized.

Other studies have focused on genes inducibly regulated, e.g. genes encoding serine proteinase inhibitors, which are expressed in response to wounding in tomato (Graham et al., *J. Biol. Chem.* (1985) 260:6555–6560; Graham et al., *J. Biol. Chem.* (1985) 260:6561–6554) and on MRNAS correlated with ethylene synthesis in ripening fruit and leaves after wounding (Smith et al., *Planta* (1986) 168: 94–100). Accumulation of a metallocarboxypeptidase inhibitor protein has been reported in leaves of wounded potato plants (Graham et al., *Biochem Biophys Res Comm* (1981) 101:1164–1170).

Agrobacterium-mediated cotton transformation is described in Urnbeck, U.S. Pat. Nos. 5,004,863 and 5,159,135 and cotton transformation by particle bombardment is reported in WO 92/15675, published Sep. 17, 1992. Transformation of Brassica has been described by Radke et al. (Theor. Appl. Genet. (1988) 75;685–694; Plant Cell Reports (1992) 11:499–505.

Transformation of cultivated tomato is described by McCormick et al., *Plant Cell Reports* (1986) 5:81–89 and Fillatti et al., *Bio/Technology* (1987) 5:726–730.

SUMMARY OF THE INVENTION

Novel recombinant geminivirus constructs including expression cassettes and transfer vectors are provided which allow for controlled transcription and/or expression in a transfected plant cell of proteins nonindigenous to the geminivirus. Also provided are methods of making the expression cassettes and methods of using them to produce transfected plant cells having an altered genotype and/or phenotype. The expression cassettes include a transactivatable expression cassette and a transacting expression cassette which may be combined in a binary plasmid. The transactivatable expression cassette has as operably linked components a transcription initiation unit obtainable from a geminivirus coat protein gene, a nucleic acid fragment other than a full length coding sequence of the geminivirus coat protein gene, and a transcription termination region. The transacting expression cassette has as operably linked components a transcription initiation unit obtainable from a 5' non-coding region of a gene which is expressed other than constitutively in one or more plant cell types, tissues, or parts, a DNA fragment comprising a coding sequence from a geminivirus gene encoding a transacting regulatory protein and a transcription termination region. A transfected plant cell may be produced by contacting a plant cell with a recombinant geminivirus transfer vector, where the transfer vector may comprise a combination of the transacting and the transactivatable expression cassettes. Alternatively, a combination of transfer vectors may be used, for example, a geminivirus having a genome in which the equivalent of the ACMV AC2 gene of DNA A has been inactivated and at least a portion of the coding sequence of the mat protein gene in the genome has been replaced with a nucleic acid fragment nonindigenous to the geminivirus and the 5' non-coding region of the equivalent of the ACMV AC2 gene of DNA B has been replaced with a nucleic acid fragment which in combination with the coat protein 5' non-coding region comprises a transcription unit; and a transacting expression cassette.

DESCRIPTION OF THE DRAWINGS

FIG. 1 shows construction of a geminivirus based binary plasmid.

DESCRIPTION OF THE SPECIFIC EMBODIMENTS

In accordance with the subject invention, novel recombinant geminivirus constructs including transfer vectors and methods for making them and using them are described. When used to transfer a plant cell the transfer vectors provide transgenic plant cell capable of controlled transcription or expression of nucleic acid fragment in one or more plant cell types. Depending upon the nature of the regulatory sequences used in the vector, transcription or expression of the nucleic acid fragment can occur in one or more particular cell types, such as seed or embryo cells or such as pollen grains or cells derived from plant ovaries, such as cotton fibers, as compared with other plant cells; in response to a particular stimulus, such as wounding of the plant, for example by insect attack, or an environmental stress such as heat or high salinity. Plants in which particular tissues and/or plant parts have an altered phenotype may be produced by the subject method.

The constructs include several forms, depending upon the intended use of the construct. Thus, the constructs include vectors, trancriptional cassettes, expression cassettes and binary plasmids. Two basic constructs are required which then may be combined in a variety of ways for transfecting a plant cell and obtaining a transgenic plant cell capable of controlled transcription or expression of a nucleic acid fragment. These two constructs include a transactivatable expression cassette and a transacting expression cassette.

The transactivatable expression cassette has as operably linked components a transcription initiation unit obtainable from a geminivirus coat protein gene, a nucleic acid fragment other than a full length coding sequence of the geminivirus coat protein gene, and a transcription termination region. The expression cassette can be prepared by replacing the native coding region of the coat protein gene with a nucleic acid fragment which is other than a full length coding sequence of the geminivirus coat protein gene, particularly a coding sequence nonindigenous to the geminivirus which is the source of the coat protein gene.

The "transcription initiation unit" comprises a geminivirus genome fragment obtainable from the 5' non-coding region of a coat protein gene wherein the fragment is of a size and nucleic acid sequence sufficient to provide for transcription of the operably linked nucleic acid fragment following activation by a geminivirus transactivating regulatory protein. By "obtainable" is intended a transcription initiation unit having a DNA sequence sufficiently similar to that of a native geminivirus coat protein transcription initiation unit to provide for transcription of the operably linked nucleic acid fragment following activation by a geminivirus transactivating regulatory protein which activates transcription from the native sequence. Obtainable includes both natural and synthetic sequences as well as sequences which may be a combination of synthetic and natural sequences. The term "nonindigenous coding sequence" means a coding sequence which does not occur in the unmodified genome of the specific geminivirus which is used for preparation of compositions of the claimed invention. A modified geminivirus coding sequence, whether modified by mutation, truncation, joining to other sequences, and the like, including a sequence other than a full length coding sequence constitutes a nonindigenous coding sequence.

The transacting expression cassette has as operably linked components a transcription initiation unit obtainable from a 5' non-coding region of a gene which is expressed other than constitutively in one or more plant cell types, plant tissues, or plant parts; a DNA fragment comprising a coding sequence from a geminivirus gene encoding a transacting regulatory protein or a congener thereof having the same or similar transactivating activity; and a transcription termination region.

For transfection, the-transactivatable expression cassette and the transacting cassette may be combined to form a binary plasmid or the two expression cassettes may be introduced into a cell on separate plasmids. By "a gene which is expressed other than constitutively" is intended a gene transcription of which is controlled, either positively or negatively, as to time, for example relative to a stage of tissue development such as preanthesis to fruit ripening in an ovary cell, and/or tissue of transcription, for example preferentially in fruit as compared to leaves.

The transfer vector is prepared by making a further modification to the viral genome. The coding sequence of the coat protein gene is replaced with a restriction site into which a nucleic acid fragment for transcription or expression may be cloned. This transfer vector can be combined with the transacting cassette on a binary vector or be introduced into cells on separate plasmids.

A further autonomously replicating transfer vector can be constructed from a modified geminivirus in which the coding region for the coat protein is replaced by a restriction site into which a nucleic acid fragment for transcription or expression may be cloned, and in which a 5'-noncoding region from a gene which is expressed other than constitutively is inserted preferably 3' to the AC1 coding region and 5' to the AC2 coding region to allow for controlled expression of the AC2 gene. For expression of an active AC2, resconstruction of the part of the AC2 coding region encompassed in the AC1 coding region may be required. The autonomously replicating vector may be transferred into plants alone or as part of a binary vector.

As a source for a modified geminivirus genome for preparation of an autonomously replicating geminivirus transfer vector or for geminivirus DNA fragments comprising a transacting regulatory protein coding sequence or a transcriptional initiation unit from a coat protein gene, any geminivirus genome may be used. The geminivirus genome fragments used for preparation of the transacting and trans-activatable expression cassettes may be from the same virus or different viruses so long as the transactivating regulatory protein and the coat protein transcription unit are capable of interacting to provide for transcription of the nucleic acid fragment operatively linked to the coat protein transcription unit. Examples of suitable geminiviruses included ACMV, TGMV, potato yellow mosaic virus, BGMV, beet curly top and squash leaf curl. Harrison (1985) *Ann. Rev. Phytopath.* 23:55–82.

The transactivating expression cassette provides for controlled expression of the transacting regulatory protein by use of a sufficient portion of a 5' non-coding region obtainable from a gene which is expressed other than constitutively in a plant cell to provide for expression of the coding sequence for the transacting regulatory protein to which it is operably linked. The transcriptional and translational initiation region (also sometimes referred to as a "promoter,") preferably comprises a transcriptional initiation regulatory region and a translational initiation regulatory region of untranslated 5' sequences, "ribosome binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

The regulatory regions are capable of directing controlled expression of a geminivirus transacting regulatory protein. By "controlled expression" is intended expression that occurs in one or a few types of plant cells, and not at all or at low levels in other cells. The expression may be as a result of a developmental change or an external stimulus or other change which results in the turning on or off of expression of particular genes in a limited number of cell types. A promoter which directs expression in a cell such as an ovary cell from anthesis through flowering but directs little or no expression after the initial changes which occur at the time surrounding pollination and/or fertilization or in other plant tissues is an example of a regulatory region capable of directing controlled expression. Other examples include a promoter which directs expression in leaf cells following damage to the leaf, for example from chewing insects but directs little or no expression in other tissues, transcriptional regulatory regions from patatin as an example for modification of expression tubers, and promoters that direct increased expression in response to environmental stimuli such as increased salinity of the agrisphere, and the like. In some embodiments, it will be desired to selectively regulate expression in a particular tissue or tissues. For example, selective regulation of expression in seed tissue, including embryo and seed coat tissue is desired for modification of seed products, including seed oils, starch, and storage proteins. For seed oil modification, a variety of phenotype alterations are of interest. These include modifying the fatty acid composition of seed oil, such as changing the ratio and/or amounts of the various fatty acids, as to chain length, degree of saturation, and the like. These results can be achieved by providing for reduction of expression of one or more endogenous products, particularly enzymes or cofactors, by producing a transcription product which is complementary to the transcription product of a native gene, so as to inhibit the expression of the gene product, or providing for expression of a gene, either endogenous or exogenous, associated with fatty acid synthesis. Of particular interest are transcriptional initiation regions associated with storage proteins, such as napin, cruciferin, β-conglycinin, phaseolin, zein or oil bodies, such as oleosin, or genes involved in fatty acid biosynthesis, including acyl carrier protein (ACP), stearoyl-ACP desaturase, and fatty acid synthases, and other genes expressed during embryo development, such as Bce4. For example, the ACP promoter provides an appropriate timing pattern for fatty acid biosynthesis modification, and the methods described herein may be used to increase the level of transcription or expression of a desired gene product over that particular period of ACP expression.

For example, when used in conjunction with a 5' untranslated sequence capable of initiating translation, expression in defined ovary tissue, including ovary integuments (also known as "ovule epidermal cells"), core or pericarp tissue, and the like, the transcriptional initiation region can direct a desired message encoded by a DNA sequence of interest in a particular tissue to more efficiently effect a desired phenotypic modification. For example, expression in ovary pericarp tissue, also known as the ovary wall and/or ovary core tissue, could result in useful modifications to the edible portions of many fruits, including true berries such as tomato, grape, blueberry, cranberry, currant, and eggplant; stone fruits (drupes), such as cherry, plum, apricot, peach, nectarine and avocado; and compound fruits (druplets), such as raspberry and blackberry. In hesperidium (oranges, citrus), such expression cassettes are expected to be expressed in the "juicy" portion of the fruit. In pepos, (such as watermelon, cantaloupe, honeydew, cucumber, and squash) the equivalent tissue is most likely the inner edible portions. In other fruits, such as legumes, the equivalent tissue is the seed pod.

The modification of analogous structures of non-edible fruit may also be of interest. Thus, of special interest are transcription initiation regions expressible in at least ovary outer pericarp tissue. For example, in cotton the analogous ovary structure is the burr of the cotton boll, in rapeseed it is the seed pod. In a like manner, regulating expression in ovary integuments and/or core tissue may result in useful modifications to the analogous fruit and related structures evolving therefrom, for example seed coat hairs, such as cotton fibers. Cotton fiber is a differentiated single epidermal cell of the outer integument of the ovule. It has four distinct growth phases; initiation, elongation (primary cell wall synthesis), secondary cell wall synthesis, and maturation. Initiation of fiber development appears to be triggered by hormones. The primary cell wall is laid down during the elongation phase, lasting up to 25 days postanthesis (DPA). Synthesis of the secondary wall commences prior to the cessation of the elongation phase and continues to approximately 40 DPA, forming a wall of almost pure cellulose. In addition to ovary tissue promoters, transcriptional initiation regions from genes expressed preferentially in seed tissues, and in particular seed coat tissues, are also of interest for applications where modification of cotton fiber cells is considered.

An example of a gene which is expressed at high levels in Brassica seed coat cells is the EA9 gene described in EPA 0 255 378. The nucleic acid sequence of a portion of the EA9 cDNA is provided therein, and can be used to obtain corresponding sequences, including the promoter region. An additional seed gene which is expressed in seed embryo and seed coat cells is the Bce4 Brassica gene. The promoter region from this gene also finds use in the subject invention; this gene and the corresponding promoter region are described in WO 91/13980, which was published Sep. 19, 1991. Fiber specific proteins are developmentally regulated. Thus, transcriptional initiation regions from proteins expressed in fiber cells are also of interest. An example of a developmentally regulated fiber cell protein, is E6 (John and Crow Proc. Nat. Acad. Sci. (USA)(1992) 89:5769–5773). The E6 gene is most active in fiber, although low levels of transcripts are found in leaf, ovule and flower.

To obtain a specifically derived transcriptional initiation region, the following steps may be employed. Messenger RNA (mRNA) is isolated from tissue of the desired developmental stage. This mRNA is then used to construct cDNA clones which correspond to the mRNA population both in terms of primary DNA sequence of the clones and in terms of abundance of different clones in the population. mRNA is also isolated from tissue of a different developmental stage in which the target gene should not be expressed (alternate tissue). Radioactive cDNA from the desired tissue and from the alternate tissue is used to screen duplicate copies of the cDNA clones. The preliminary screen allows for classification of the cDNA clones as those which correspond to mRNAs which are abundant in both tissues; those which correspond to mRNAs which are not abundant in either tissue; those which correspond to mRNAs which are abundant in one tissue and relatively non-abundant in the other. Clones are then selected which correspond to mRNAs that are abundant only in the desired tissue and then these selected clones are further characterized.

Since the hybridization probe for the preliminary screen outlined above is total cDNA from a particular tissue, it hybridizes primarily to the most abundant sequences. In order to determine the actual level of expression, particularly in tissue where the mRNA is not as abundant, the cloned sequence is used as a hybridization probe to the total mRNA population(s) of the desired tissue(s) and various undesired tissue(s). This is most commonly done as a Northern blot which gives information about both the relative abundance of the mRNA in particular tissues and the size of the mRNA transcript.

It is important to know whether the abundance of the mRNA is due to transcription from a single gene or whether it is the product of transcription from a family of genes. This can be determined by probing a genomic Southern blot with the cDNA clone. Total genomic DNA is digested with a variety of restriction enzymes and hybridized with the radioactive cDNA clone. From the pattern and intensity of the hybridization, one can distinguish between the possibilities that the mRNA is encoded either by one or two genes or by a large family of related genes. It can be difficult to determine which of several cross-hybridizing genes encodes the abundantly expressed mRNA found in the desired tissue. In this case it is important to use a probe which is capable of distinguishing a particular gene from the remainder of the family members.

The cDNA obtained as described can be sequenced to determine the open reading frame (probable protein-coding region) and the direction of transcription so that a desired target DNA sequence later can be inserted at the correct site and in the correct orientation into a transcription cassette. Sequence information for the cDNA clone also facilitates characterization of corresponding genomic clones including mapping and subcloning as described below. At the same time, a genomic library can be screened for clones containing the complete gene sequence including the control region flanking the transcribed sequences. Genomic clones generally contain large segments of DNA (approximately 10–20 kb) and can be mapped using restriction enzymes, then subcloned and partially sequenced to determine which segments contain the developmentally regulated gene.

Using the method described above, several transcriptional regulatory regions have been identified. One example is the tomato-derived transcriptional initiation region which regulates expression of the sequence corresponding to the pZ130 cDNA clone. Sequences hybridizable to the pZ130 clone, for example, probe pZ7, show abundant mRNA, especially at the early stages of anthesis. The message is expressed in ovary integument and ovary outer pericarp tissue and is not expressed, or at least is not readily detectable, in other tissues or at any other stage of fruit development. Thus, the pZ130 transcriptional initiation region is considered ovary-specific for purposes of this invention. The pZ130 transcriptional initiation region is described in U.S. Pat. No. 5,175,095, which disclosure is incorporated herein by reference.

A promoter from a tomato gene, referred to as 2A11, was isolated using the methods described above. The 2A11 promoter provides for an abundant messenger, being activated at or shortly after anthesis and remaining active until the red fruit stage. Expression of the 2A11 gene under the 2A11 promoter occurs only in fruit; generally no detectable expression is obtained in root, leaves or stems. The gene encodes a sulfur-rich amino acid sequence similar to plant storage proteins in sulfur content and size. The 2A11 transcriptional initiation region is described in U.S. Pat. No. 4,943,674 issued Jul. 24, 1990 and in PCT application WO90/04063 which disclosures are hereby incorporated by reference.

Tissue-specific transcription suggests that gene regulatory proteins may be bound to enhancer sequences and other upstream promoter elements in specific cells. By enhancer element ("enhancer") is intended a regulatory DNA sequence that is capable of activating transcription from a promoter linked to it with synthesis beginning at the normal RNA start site; which is capable of operating in both orientations (normal or flipped); and which is capable of functioning even when moved either upstream or downstream from the promoter. Both enhancers and other upstream promoter elements bind sequence specific DNA-binding proteins that mediate their effects.

As an example, to identify the exact nucleotide sequences important for the function of the enhancer(s), and other upstream elements, fragments of the 2A11 5'-region are screened for their capacity to bind nuclear proteins and for their ability to function in a heterologous promoter. Binding experiments with nuclear proteins from fruit-tissue and other tissue such as leaf can be used to determine the presence of enhancer and silencer sequences; the protein binding studies can be used to pinpoint specific nucleotide sequences that bind to a corresponding series of gene regulatory proteins.

The activity of each enhancer and other upstream promoter elements generally is present on a segment of DNA which may contain binding sites for multiple proteins. The binding sites can generally be dissected by preparing smaller mutated versions of the enhancer sequence joined to a reporter gene whose product is easily measured, such as the Gus gene. The effect of each mutation on transcription can then be tested. Alternatively, fragments of this region can be prepared. Each of the mutated versions of the enhancer sequence or the fragments can be introduced into an appropriate host cell and the efficiency of expression of the reporter gene measured. Those nucleotides required for enhancer function in this test are then identified as binding sites for specific proteins by means of gel mobility shift and DNA footprinting studies. An alternate means of examining the capability of the isolated fragments to enhance expression of the reporter gene is to look for sub-domains of the upstream region that are able to enhance expression levels from a promoter which comprises the TATA CAAT box but shows little or no detectable activity. An example of such a promoter is the truncated 35S promoter (see for example Poulsen and Chua, Mol. Gen. Genet. (1988) 214:16–23 and Benfey, et al., EMBO J. (1990) 9:1677–1684 and 1685–1696 and Gilmartin, Plant Cell (1990) 2:369–378). A fragment of the 5'-region is inserted in front of the truncated promoter in an expression cassette, and the effect on expression of the reporter gene evaluated. PCT application WO90/04063 which disclosure is hereby incorporated by reference discloses how to make and how to use upstream regulatory sequences as exemplified using the 2A11 gene.

Other promoter regions of interest include those which regulate expression of the enzyme polygalacturonase, an enzyme which plays an important role in fruit ripening. The polygalacturonase promoter is active in at least the breaker through red fruit stage. In determining optimum amounts of other 5' regions, such as that from the PG gene, which are required to give expression of a DNA sequence of interest preferentially in fruit, screening can be carried out as described above for the 2A11 5' region, using a reporter gene such as Gus. The polygalacturonase gene is described in U.S. Pat. No. 4,535,060 issued Aug. 13, 1985, U.S. Pat. No. 4,769,061 issued Sep. 6, 1988, U.S. Pat. No. 4,801,590 issued Jan. 31, 1989 and U.S. Pat. No. 5,107,065 issued Apr. 21, 1992, which disclosures are incorporated herein by reference.

Also of interest are 5' non-coding regions from the following genes: elongation factor EF-1, which is active in meristematic tissue, and is disclosed in U.S. Pat. No. 5,177,010 issued Jan. 5, 1993; MAC, which is disclosed in U.S. Pat. No. 5,106,739 which issued Apr. 21, 1992; heat shock, disclosed in U.S. Pat. No. 5,187,267 issued Feb. 16, 1993; and ACC/napin which is active in seed and is disclosed in EP 255 378. The cited patents and applications are incorporated herein by reference.

A transcriptional transactivatable cassette will include as operably linked components in the direction of transcription, geminivirus coat protein transcriptional initiation region and optionally a translational initiation region, a nucleic acid sequence of interest, and a transcriptional and optionally a translational termination region functional in a plant cell. When the cassette provides for the transcription and translation of a nucleic acid sequence of interest it is considered an expression cassette. One or more introns may be also be present in the cassette. Other sequences may also be present in the transactivatable cassette, including those encoding transit peptides and secretory leader sequences as desired. How to obtain and use these sequences are well known to those skilled in the art.

Downstream from, and under the regulatory control of, the coat protein transcriptional/translational initiation control region is a nucleotide sequence of interest. The nucleotide sequence may be any open reading frame encoding a polypeptide of interest, for example, an enzyme, or a sequence complementary to a genomic sequence, where the genomic sequence may be an open reading frame, an intron, a noncoding leader sequence, or any other sequence where the complementary sequence inhibits transcription, messenger RNA processing, for example, splicing, or translation. The nucleotide sequences of this invention may be synthetic, naturally derived, or combinations thereof. Depending upon the nature of the nucleotide sequence of interest, it may be desirable to synthesize the sequence with plant preferred codons. The plant preferred codons may be determined from the codons of highest frequency in the proteins expressed in the largest amount in the particular plant species of interest.

Phenotypic modification can be achieved by modulating production either of an endogenous transcription or translation product, for example as to the amount, relative distribution, or the like, or an exogenous transcription or translation product, for example to provide for a novel function or products in a transgenic host cell or tissue. Of particular interest are DNA sequences encoding expression products associated with the development of plant fruit, including genes involved in metabolism of cytokinins, auxins, ethylene, abscissic acid, and the like. Methods and compositions for modulating cytokinin expression are described in U.S. Pat. No. 5,177,307, which disclosure is hereby incorporated by reference. Alternatively, various genes, from sources including other eukaryotic or prokaryotic cells, including bacteria, such as those from *Agrobacterium tumefaciens* T-DNA auxin and cytokinin biosynthetic gene products, for example, and mammals, for example interferons, may be used. Other genes of interest include fatty acid biosynthesis genes including medium and long-chain thioesterases (WO 91/16421 published Oct. 31, 1991), desaturase (WO 91/13972 published Sep. 19, 1991), synthases (WO 92/03564, published Mar. 5, 1992); flavor genes such as SPS (WO 91/19808, published Dec. 26, 1991); and ripening genes, such as anti sense polygalacturonase (U.S. Pat. No. 4,801,540), anti-sense ethylene genes such as ACCD, ACC synthase, ethylene forming enzyme (EFE) (WO 91/02958). Other phenotypic modifications include modification of the color of plant parts developing from ovary integuments and/or core tissue, for example seed coat hairs, such as cotton fibers. Of interest are genes involved in production of melanin and genes involved in the production of indigo. Melanins are dark brown pigments found in animals, plants and microorganisms, any of which may serve as a source for sequences for insertion into the constructs of the present invention. Color in cotton and color and fruit quality may be modified by the use of carotenoid pathway genes (EP 0 393 690 and WO 91/13078).

Transactivatable transcriptional cassettes may be used when the transcription of an anti-sense sequence is desired. When the expression of a polypeptide is desired, transactivatable expression cassettes providing for transcription and translation of the nucleotide sequence of interest will be used. Various changes are of interest; these changes may include modulation (increase or decrease) of formation of particular saccharides, hormones, enzymes, or other biological parameters. These also include modifying the composition of the final fruit or fiber, for example changing the ratio and/or amounts of water, solids, fiber or sugars. Desirable seed modifications includ oil content, fatty acid composition, and storage protein content. Other phenotypic properties of interest for modification include response to stress, organisms, herbicides, brushing, growth regulators, and the like. These results can be achieved by providing for reduction of expression of one or more endogenous products, particularly an enzyme or cofactor, either by producing a transcription product which is complementary (anti-sense) to the transcription product of a native gene, so as to inhibit the maturation and/or expression of the transcription product, or by providing for expression of a gene, either endogenous or exogenous, to be associated with the development of a particular tissue or plant part.

The termination region which is employed in the transactivatable and transacting expression cassettes will be primarily those which are of convenience, since the termination regions appear to be relatively interchangeable. The termination region which is used may be native with the transcriptional initiation region, may be native with the DNA sequence of interest, may be derived from another source. The termination region may be naturally occurring, or wholly or partially synthetic. Convenient termination regions are available from the Ti-plasmid of *A. tumefaciens*, such as the octopine synthase and nopaline synthase termination regions. In some embodiments, it may be desired to use the 3' termination region native to the transcription initiation region used in a particular construct.

The various constructs normally will be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed cells as compared to cells lacking the DNA which has been introduced. Components of DNA constructs including transcription cassettes of this invention may be prepared from sequences which are native (endogenous) or foreign (exogenous) to the host. By foreign is intended that the sequence is not found in the wild-type host into which the construct is introduced. Heterologous constructs will contain at least one region which is not native to the gene from which the transcription initiation region is derived.

In preparing the constructs, the various DNA fragments may be manipulated, so as to provide for DNA sequences in the proper orientation and, as appropriate, in proper reading frame for expression; adapters or linkers may be employed for joining the DNA fragments or other manipulations may be involved to provide for convenient restriction sites, removal of superfluous DNA, removal of restriction sites, or the like. In vitro mutagenesis, primer repair, restriction, annealing, resection, ligation, or the like may be employed, where insertions, deletions or substitutions, e.g. transitions and transversions, may be involved. Conveniently, a vector or cassette may include a multiple cloning site downstream from the ovary-related transcription initiation region, so that the construct may be employed for a variety of sequences in an efficient manner.

In carrying out the various steps, cloning is employed, so as to amplify the amount of DNA and to allow for analyzing the DNA to ensure that the operations have occurred in proper manner. By appropriate manipulations, such as restriction, chewing back or filling in overhangs to provide blunt ends, ligation of linkers, or the like, complementary ends of the fragments can be provided for joining and ligation. A wide variety of cloning vectors are available, where the cloning vector includes a replication system functional in *E. coli* and a marker which allows for selection of the transformed cell. Illustrative vectors include pBR332, pUG series, M13mp series, pACYC184, etc. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence. Each of the partial constructs may be cloned in the same or different plasmids.

A variety of techniques are available and known to those skilled in the art for introduction of constructs into a plant cell host. These techniques include transfection with DNA employing *A. tumefaciens* or *A. rhizogenes* as the transfecting agent, protoplast fusion, injection, electroporation, particle acceleration, etc. For transformation with Agrobacterium, plasmids can be prepared in *E. coli* which contain DNA homologous with the Ti-plasmid, particularly T-DNA. The plasmid may or may not be capable of replication in Agrobacterium, that is, it may or may not have a broad spectrum prokaryotic replication system such as does, for example, pRK290, depending in part upon whether the transcription cassette is to be integrated into the Ti-plasmid or to be retained on an independent plasmid. The Agrobacterium host will contain a plasmid having the vir genes necessary for transfer of the T-DNA to the plant cell and may or may not have the complete T-DNA. At least the right border and frequently both the right and left borders of the T-DNA of the Ti- or Ri-plasmids will be joined as flanking regions to the transcription construct. The use of T-DNA for transformation of plant cells has received extensive study and is amply described in EPA Ser. No. 120,516, Hoekema, In: The Binary Plant Vector System Offset-drukkerij Kanters B. V., Alblasserdam. 1985. Chapter V, Knauf, et al., Genetic Analysis of Host Range Expression by Agrobacterium, In: Molecular Genetics of the Bacteria-Plant Interaction, Puhler, A. ed., Springer-Verlag. N.Y., 1983, p. 245, and An, et al., EMBO J. (1985) 4:277–284.

For infection, particle acceleration and electroporation, a disarmed Ti-plasmid lacking particularly the tumor genes found in the T-DNA region) may be introduced into the plant cell. By means of a helper plasmid, the construct may be transferred to the *A. tumefaciens* and the resulting transfected organism used for transfecting a plant cell; explants may be cultivated with transformed *A. tumefaciens* or *A. rhizogenes* to allow for transfer of the transcription cassette to the plant cells. Alternatively, to enhance integration into the plant genome, terminal repeats of transposons may be used as borders in conjunction with a transposase. In this situation, expression of the transposase should be inducible, so that once the transcription construct is integrated into the genome, it should be relatively stably integrated. Transgenic plant cells are then placed in an appropriate selective medium for selection of transgenic cells which are then grown to callus, shoots grown and plantlets generated from the shoot by growing in rooting medium.

To confirm the presence of the transgenes in transgenic cells and plants, a Southern blot analysis can be performed using methods known to those skilled in the art. Expression products of the transgenes can be detected in any of a variety of ways, depending upon the nature of the product, and include immune assay, enzyme assay or visual inspection, for example to detect pigment formation in the appropriate plant part or cells. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics. The terms transgenic plants and transgenic cells include plants and cells derived from either transgenic plants or transgenic cells.

The various sequences provided herein may be used as molecular probes for the isolation of other sequences which may be useful in the present invention, for example, to obtain related transcriptional initiation regions from the same or different plant sources. Related 5'non-coding regions obtainable from the sequences provided in this invention will show at least about 60% homology, and more preferred regions will demonstrate an even greater percentage of homology with the probes. Of particular importance is the ability to obtain related transcription initiation control regions having the timing and tissue parameters described herein. For example, using the probe pZ130, at least 7 additional clones, have been identified, but not further characterized. Thus, by employing the techniques described in this application, and other techniques known in the art (such as Maniatis, et al., *Molecular Cloning; A Laboratory Manual* (Cold Spring Harbor, N.Y.) 1982), other transcription initiation regions capable of controlled direction of transcription and/or expression as described in this invention may be determined. The constructs can also be used in conjunction with plant regeneration systems to obtain plant cells and plants; the constructs may also be used to modify the phenotype of plant tissues and plant parts produced thereby.

The invention finds particular use in controlling transcription or expression of a nucleic acid fragment so as to provide for preferential or at least substantially specific expression in a particular tissue, for example in fruit or seeds as compared to other tissues such as leaf, stems or roots. By "at least substantially" is intended that expression of a nucleic acid fragment of interest in the particular tissue or tissues or parts is greater by about 100 fold the expression of the nucleic acid fragment in other tissues or parts of the plant. By "fruit" is intended the ripened ovary wall of a flower and any other closely associated parts. (See Weirer, T. E. et al., ed., Botany: An Introduction to Plant Biology (6th ed.) (John Wiley & Sons, 1982); Tootill & Backmore, eds., The Facts on a File Dictionary of Botany (Market Home Boob Ltd., 1984). The following examples are offered by way of illustration and not by limitation.

EXAMPLES

EXAMPLE 1

Preparation of ACMV Expression Cassettes

The complete nucleotide sequences of ACMV (formerly called CLV) DNA 1 and DNA 2 are published (Stanley and Gay, 1983, Nature 301,260–262). To construct a binary vector for plant transformation containing the viral trans-acting factor AC2 under the control of the ACP regulatory elements, a C12-specific thioesterase from bay laurel under the control of the vital coat protein regulatory elements and a kanamycin resistance gene under the control of the CaMV 35s promoter, the following constructs are made.

The coat protein (AV1) regulatory sequences (labeled CP5' and CP3') were obtained by PCR using the following oligonucleotides and pETA092 as a template. pETA092 (obtained from J. Stanley, John Innes Inst., Norwich, UK), is a complete clone of ACMV DNA 1 in the Mlu1 site of the cloning vector pIB120 (International Biotechnologies, Inc., New Haven, Conn.). The oligonucleotides for the coat protein 5' were #3558, 5'-CTGGAGCTCATGTFGACCAAGTCAATFGG-3'(SEQ ID NO. 1) and #3560, 5'-GCTACTAGTGGATCCCACATTGCGC-3'(SEQ ID NO. 2) and were designed to amplify the ACMV DNA 1 sequences between nucleotides 2752 and 299 which includes the common region and the coat protein transcription start site. Oligonucleotide #3558 incorporates a Sac1 restriction site at the 5'-end of the PCR fragment and oligo #3560 incorporates a Spe1 site at the 3'-end of the fragment for subcloning. The 3'oligonucleotides were #3564, 5'CCACTGCAGCGACGTTGAAAATACG-3'(SEQ ID NO. 3) and 3559, 5'-CACACTAGTCAATGTAATTAGAGCTGC-3'(SEQ ID NO. 4). They were designed to amplify ACMV DNA1 from nucleotides 1175 to 1315 with a Pst1 and Spe1 site on the 5' and 3'-ends of the fragment respectively. This fragment contains the potential polyadenylation signal for the coat protein gene. The PCR conditions were: 94 degrees Centigrade, 10 min, 72 degrees Centigrade, 7 min, for addition of the Taq polymerase, then thirty cycles of 94 degrees Centigrade for 15 sec, 50 degrees Centigrade for 30 sec, and 72 degrees Centigrade for 30 sec.

The coat protein 3' sequences were subcloned from the PCR reaction (described above) to create pCGN3289 by cutting the PCR DNA with Pst 1 and Spe 1 and ligation to a modified chloramphenicol resistant pCGN565 (pCGN3288) also cut with Pst1 and Spe1. pCGN3288 was constructed by digestion of pCGN565 (described in other patent applications) with HindIII and Pst1 and ligation of a synthetic linker containing HindIII, Spe1 and Pst1 sites. The linker was made by annealing the synthetic oligonucleotides 5'-AGCTTCCACTAGTGGCTGCA-3'(SEQ ID No. 5) and 5'-GCCACTAGTCCA-3'(SEQ ID NO. 6). Bay laurel thioesterase coding sequence was isolated from pCGN3826 (described in CGN82-4WO patent application) by a BamH1 complete and Pst 1 partial digestion. The isolated 1.27 kb thioesterase sequence was then cloned upstream of the coat protein 3 by ligation of the isolated thioesterase fragment with pCGN3289 digested with BamH1 and Pst1. The plasmid containing the thioesterase sequences and the CP3' is named pCGN3291.

The coat protein 5'-sequence was subcloned from the PCR DNA by digestion with SacI and Spe1 and ligation to a modified Bluescript II KS(−) vector (Stratagene, La Jolla, Calif.) named pCGN3290 cut with Sac1 and Spe1. pCGN 3290 was made by digestion of pBluescript II KS(−) with BAMH1 and Spe1 and ligation with pCGN3291 cut with BamH1 and Spe1. The resulting plasmid contains an expression cassette consisting of the CP5', the thioesterase gene, and the CP 3' in an ampicillin resistant backbone.

The AC2 open reading frame was obtained by PCR using primers with the following sequences: 5'-TGCTGAATTCAGAATGCAATCTFCATCACCC-3' (SEQ ID NO. 7) and 5'-TGCTCTGCAGCTAAAGACCCTTAAGAAAAGACC-3'(SEQ ID NO. 8) corresponding to nucleotides 1774 to 1754 surrounding the ATG start codon of the AC2 open reading frame and nucleotides 1386 to 1364 surrounding the stop codon. The primers have EcoR1 and Pst1 sites respectively on the ends for further cloning steps. The template for the PCR was 30 cycles, then 10 min at 72 degrees Centigrade. The resulting PCR fragment (410 bp) was subcloned into pBluescript II SK(−) by digestion with EcoR1 and Pst1. The AC2 open reading frame is inserted in the ACP expression cassette, pCGN1977 (Soberer et al., 1992, Plant Molecular Biology 18, 591–594), by digestion with EcoR1 and Pst1 and ligation to pCGN1977 cut with EcoR1 and Pst1.

The CP 5'/TE/CP 3' cassette is combined with the ACP 5'/AC2/ACP3'cassette by respective digestion with Sac1 and Spe1 and Asp718 and Sac1 and ligation of the plasmids with an Asp718 and Xbal cut binary vector such as pC2GN1557 (McBride and Summerfelt, 1990, Plant Molecular Biology 14, 269–276). The resulting binary vector contains: the left border—35s/NPT11/tm1-ACP5'/AC2/ACP3 -CP 5'/TE/ CP3' right border expression cassette in a gentamicin resistant background. The binary vector can be transformed into Agrobacterium tumefaciens and used to produce Brassica plants.

The above invention relates to the use of geminivirus vectors to provide for controlled expression of a nucleic acid fragment by using the 5'coding region from genes which provide for developmental regulation in plant cells in place of the native promoter of the geminivirus gene encoding a transacting regulatory protein. In this way, the transcription cassettes and expression cassettes can be produced which allow for differentiated cell production of the desired product from the coat protein promoter of the geminivirus. Thus, the phenotype of a particular plant part may be modified, without requiring that the regulated product be produced in all tissues, which may result in various adverse effects on the growth, health, and production capabilities of the plant. Particularly, tissue specific transcription initiation capability is provided for modifying the phenotypic properties of a variety of tissues.

All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A geminivirus transfer vector comprising a geminivirus genome wherein the coding sequence for the coat protein gene in said genome is deleted and replaced with a first multiple cloning site and wherein the transcriptional initiation region of the geminivirus transacting factor gene in said genome is replaced with a second multiple cloning site.

2. The vector of claim 1, wherein a DNA sequence encoding a transcriptional initiation region of a gene which is expressed other than constitutively in one or more plant cells is inserted into said second multiple cloning site.

3. The vector of claim 1, wherein a DNA sequence of interest is inserted into said first multiple cloning site.

4. The vector of claim 1, wherein said geminivirus genome is repeated at least 1.2 times.

5. The vector of claim 1, wherein said geminivirus is an African cassava mosaic virus.

6. A plant cell comprising a geminivirus transfer vector of claim 1.

7. The vector of claim 3, wherein expression of said DNA sequence of interest modifies a plant phenotype.

8. The vector of claim 3, wherein a transcription product of said DNA sequence of interest modifies a plant phenotype.

9. The vector of claim 4, further comprising a right T-DNA border.

10. A transacting expression cassette comprising as operatively linked components in the 5' to 3' direction of transcription:

a transcriptional initiation region obtained from a 5' non-coding region of a plant gene which is expressed other than constitutively in one or more plant cells;
a DNA fragment encoding a geminivirus coat protein transacting factor; and
a transcriptional termination region.

11. The transacting expression cassette of claim 10, wherein said plant gene which is expressed other than constitutively is a gene coding for a polypeptide selected from the group consisting of:

ACP, Bce4, napin, polygalacturonase, 2A11, pZ7, hsp80, EF-1, ssu, and EA9.

12. The transacting expression cassette of claim 10, wherein said geminivirus is an African cassava mosaic virus.

13. A plant cell comprising a transacting expression cassette of claim 10.

14. A binary plasmid comprising:

(1) A transactivatable cassette comprising a transcription initiation region obtained from a geminivirus coat protein gene; a DNA sequence of said coat protein gene, the expression of which modifies a plant phenotype; and a transcription termination region; and (2) a transacting expressing cassette comprising a transcriptional initiation region obtained from a 5' non-coding region of a plant gene which is expressed other than constitutively in one of more plant cells; a DNA fragment encoding a coat protein transacting factor; and a transcriptional termination region.

15. The binary plasmid of claim 14, further comprising a right T-DNA border.

16. The binary plasmid of claim 14, further comprising a plant selectable marker.

17. A plant cell comprising a binary plasmid of claim 14.

18. A binary vector comprising:

(1) a geminivirus genome wherein a coding sequence in a coat protein gene in said genome is deleted and replaced with a multiple cloning site and a DNA sequence encoding a geminivirus transacting factor is modified to prevent said geminivirus from producing a functional transacting factor protein;

(2) a transacting expression cassette comprising a transcriptional initiation region obtained from a 5' non-coding region of a plant gene which is expressed other than constitutively in one or more plant cells, a DNA fragment encoding a geminivirus coat protein transacting factor and a transcriptional termination region; and (3) a right T-DNA border region.

19. A method of producing a geminivirus transfer vector, said method comprising:

in a geminivirus genome, replacing a coding sequence of a coat protein gene with a DNA sequence of interest, the expression of which, modifies a plant phenotype and replacing the transcriptional initiation region of the geminivirus transacting factor gene in said genome with a DNA sequence encoding a transcriptional initiation region of a gene which is expressed other than constitutively in one or more plant cells.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: synthetic oligonucleotide ( x i ) SEQUENCE DESCRIPTION: SEQ ID NO: 1:

CTGGAGCTCA TGTTGACCAA GTCAATTGG    29

(2) INFORMATION FOR SEQ ID NO: 2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic oligonucleotide (xi) SEQUENCE DESCRIPTION: SEQ ID NO: 2:

GCTACTAGTG GATCCCACAT TGCGC    25

(2) INFORMATION FOR SEQ ID NO: 3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: synthetic oligonucleotide (xi) SEQUENCE DESCRIPTION: SEQ ID NO: 3:

CCACTGCAGC GACGTTGAAA ATACG    25

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: synthetic oligonucleotide (xi) SEQUENCE DESCRIPTION: SEQ ID NO: 4:

CACACTAGTC AATGTAATTA GAGCTGC    27

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic oligonucleotide (xi) SEQUENCE DESCRIPTION: SEQ ID NO: 5:

AGCTTCCACT AGTGGCTGCA    20

(2) INFORMATION FOR SEQ ID NO: 6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: synthetic oligonucleotide (xi) SEQUENCE DESCRIPTION: SEQ ID NO: 6:

GCCACTAGTC CA    12

(2) INFORMATION FOR SEQ ID NO: 7:

-continued ( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: synthetic oligonucleotide ( x i ) SEQUENCE DESCRIPTION: SEQ ID NO: 7:

TGCTGAATTC AGAATGCAAT CTTCATCACC C    31

( 2 ) INFORMATION FOR SEQ ID NO: 8:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: synthetic oligonucleotide ( x i ) SEQUENCE DESCRIPTION: SEQ ID NO: 8:

TGCTCTGCAG CTAAAGACCC TTAAGAAAAG ACC    33